WHITE ASH TREE
Filed June 27, 1974 2 Sheets-Sheet 1
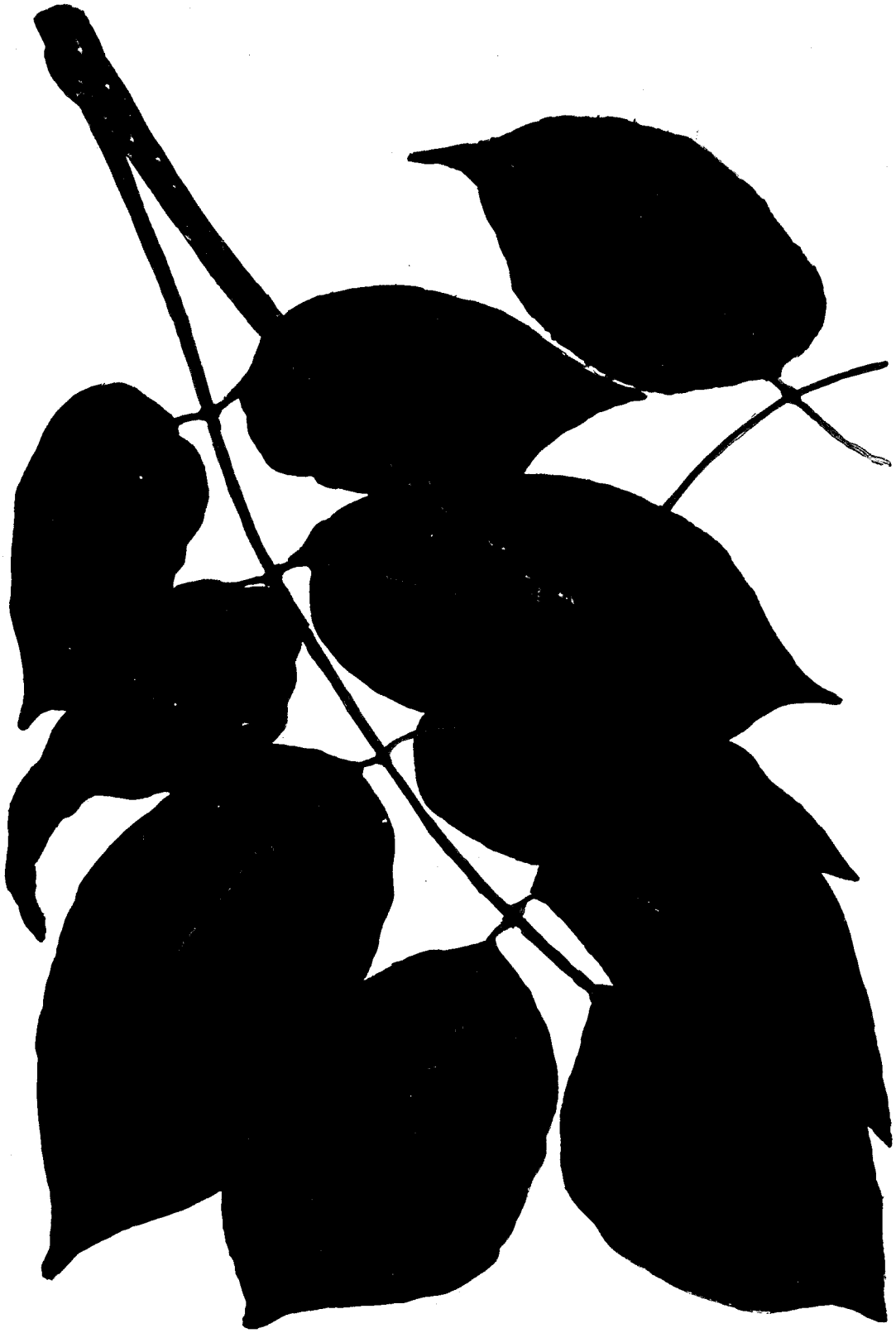

WHITE ASH TREE
Filed June 27, 1974 2 Sheets-Sheet 2
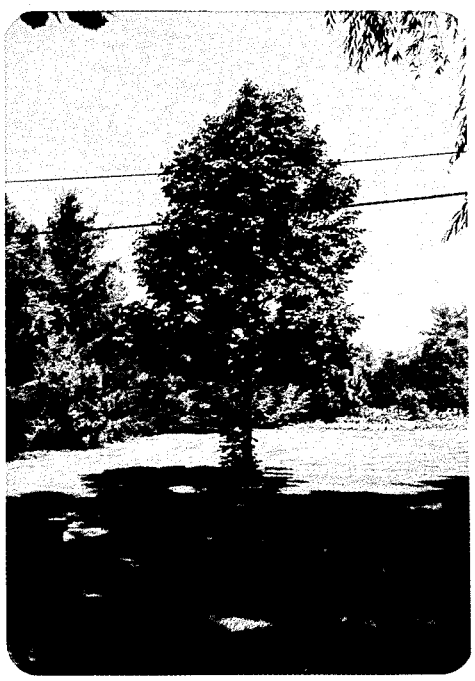

United States Patent

Plant Pat. 3,762
Patented Aug. 12, 1975

3,762

WHITE ASH TREE

Willet N. Wandell, Rte. 3, Myra Station Road, Urbana, Ill. 61801

Filed June 27, 1974, Ser. No. 483,887
Int. Cl. A01h *5/12*
U.S. Cl. Plt.—51 1 Claim

This invention relates to a new variety of *Fraxinus americana,* commonly known as white ash tree.

The new variety of the present invention is a distinct variety of white ash discovered by growing in block No. 1 of the Myra Station Road Nursery at rural Urbana, Ill.

The tree plant of the new variety was discovered several years ago, one year after a spring planting of seedlings. The new variety was an immediately noted darker green than other trees in the planting. The new variety also exhibited a more robust growing habit and larger leaflets than the other trees in the planting. As growth continued, the new variety exhibited a much more compact growth habit without trimming and pruning. This made the new variety visually outstanding from a considerable distance in the stand of other trees. Further, new leaves appearing in the spring and throughout the growing season have the characteristic of bronze and often ruby color which persists until the leaves are 50 percent developed in size.

The instant white ash variety has other distinctive characteristics, namely, a dense habit of growth and relatively shorter internodes. This makes it easier to grow the new variety than other white ashes under propagation. The leaflets are larger than average, and grow on stout petioles. The darker than average leaflets also have a somewhat leathery texture.

My novel variety of white ash is described in detail below.

FIG. 1 illustrates a black and white photograph of the mature white ash variety; and FIG. 2 illustrates the growing leaves, including a leaf with the characteristic bronze and ruby color.

The illustration of FIG. 1 shows the tree after about ten growing seasons. Such tree is robust, dense, and hardy. The following detailed description makes reference to colors, particularly as illustrated in the showing in FIG. 2. Reference to such colors is to the Royal Horticultural Colour Chart, published by the Royal Horticultural Society of London, Library Calling No. 581.4, B 77H.

The variety is propagated by budding and such asexual reproduction carries over distinguishing characteristics which further include the following.

The trunk is dark brown or gray with many close ridges crossing to form a diamond pattern.

The branches are stout and glabrous. The color is glossy green, No. 137–B. The lenticels are pale, prominent.

The foliage is characterized by leaves which are compound pinnate. The leaves range from 17 cm. to 28 cm. in length and from 13 cm. to 21 cm. in width. The leaflets are characterized by a large size ranging in number from 7 to 9, usually 7. The length of the leaflets is 8 to 14 cm. and the width is from 4.5 to 7 cm. The shape of the leaflets is ovate to ovate-lanceolate. There is a short acuminate apex. The base is cuneate to rounded. The margin of the leaflets is weakly dentate above the middle, essentially entire below the middle. The color of the leaflet is dark green above, No. 147A and pale green beneath, No. 148B. The degree of pubescence is characterized by being glabrous above and having hairy veins beneath. The petiolules are 3 to 10 mm. long and are glabrous.

No flower buds or flowers were observed after 15 years of observation.

What is claimed is:

1. The variety of white ash substantially as shown and described herein, characterized particularly by an extremely robust growing habit, larger leaflets and a stronger petiole, together with a heavy dense compact habit of growth without pruning and trimming.

No references cited.

ROBERT E. BAGWILL, Primary Examiner